(12) United States Patent
Aleotti

(10) Patent No.: US 7,989,008 B2
(45) Date of Patent: Aug. 2, 2011

(54) COSMETIC PREPARATIONS DESIGNED TO REDUCE UNSIGHTLY CELLULITE

(75) Inventor: Alberto Aleotti, Florence (IT)

(73) Assignee: Menarini Industrie Farmaceutiche Riunite S.R.L., Firenze (IT)

( * ) Notice: Subject to any disclaimer, the term of this patent is extended or adjusted under 35 U.S.C. 154(b) by 151 days.

(21) Appl. No.: 12/530,257

(22) PCT Filed: Mar. 20, 2008

(86) PCT No.: PCT/EP2008/002261
§ 371 (c)(1),
(2), (4) Date: Sep. 8, 2009

(87) PCT Pub. No.: WO2008/116602
PCT Pub. Date: Oct. 2, 2008

(65) Prior Publication Data
US 2010/0112104 A1    May 6, 2010

(30) Foreign Application Priority Data
Mar. 26, 2007    (IT) ................ MI2007A604

(51) Int. Cl.
*A01N 65/00* (2009.01)
(52) U.S. Cl. ..................................... 424/725
(58) Field of Classification Search ............... None
See application file for complete search history.

(56) References Cited

FOREIGN PATENT DOCUMENTS
WO    2006/063714 A    6/2006

OTHER PUBLICATIONS

Edmondson, Benzyl vinylogous amide substituted aryldihydropyridazinones and aryldimethylpyrazolones as potent and selective PDE3B inhibitors, Bioorganic & Medicinal Chemistry Letters, 2003, 13(22):3983-3987.

*Primary Examiner* — Michael Meller
(74) *Attorney, Agent, or Firm* — Lucas & Mercanti, LLP

(57) ABSTRACT

The invention relates to a new derivative of aryldimethylpyrazolone of formula (I) which is effective in reducing unsightly cellulite, and compositions containing it.

10 Claims, No Drawings

COSMETIC PREPARATIONS DESIGNED TO REDUCE UNSIGHTLY CELLULITE

CROSS-REFERENCE TO RELATED APPLICATIONS

This application is a 371 of PCT/EP2008/002261 filed Mar. 20, 2008, which claims the benefit of Italian Patent Application No. MI2007A604 filed Mar. 26, 2007, the contents of each of which are incorporated herein by reference.

FIELD OF INVENTION

This invention relates to a derivative of aryldimethylpyrazolone useful for the treatment of cellulite, and compositions containing it.

BACKGROUND TO THE INVENTION

Cellulite, or "oedematous-fibrosclerotic panniculopathy", is a disorder that affects the hypodermis, a tissue situated below the dermis, which has a mainly adipose nature. Cellulite almost exclusively affects women, and is suffered by approximately 80-85% of the post-adolescent female population, mostly Caucasian, especially those with the "Mediterranean" skin type.

Even slim women tend to present more marked adipose accumulations on the thighs.

Cellulite is caused by slowing of the venous and lymphatic microcirculation in the adipose tissue, leading to impairment of its most important metabolic functions and an increase in tissue toxins.

The visible consequence of this degeneration of the subcutaneous adipose tissue is fluid retention, due to fluid stagnation in the intercellular spaces, and an increase in the volume of the adipose cells.

Cellulite has a number of genetic (familial predisposition), constitutional, hormonal and vascular causes, often aggravated by a sedentary lifestyle, stress, smoking, liver disease, hormonal imbalances, incorrect diet, intestinal disorders or disorders characterised by marked fluid retention.

Cellulite is mainly a cosmetic problem, and must be considered in that light.

At present, cellulite is commonly treated with:

1. physical remedies (laser treatment, iontophoresis, ultrasound treatment and ozone treatment);
2. diet supplements: mineral salts (especially potassium), vitamins, plant extracts (which are believed to increase lipid metabolism), diuretics, bowel regulators and bioflavonoids (active on the microcirculation);
3. mesotherapy using the following active constituents: coenzyme A, phosphatidylcholine, aminophylline, escin or homeopathic products;
4. pharmacologically active products such as caffeine, aminophylline, levothyroxine and escin.

There are numerous cosmetic compositions for the treatment of cellulite on the market. They mainly contain plant extracts such as extracts of Centella asiatica, Ginkgo biloba, birch and escin, which is extracted from the horse chestnut tree.

Others contain compounds such as caffeine, β-adrenergic stimulants and methylxanthine. Their cosmetic efficacy is dubious, and the observable improvements are often due to the diet and massage associated with the application of those compositions.

EP692250 describes the use of flavones to improve the microcirculation.

GB1588501, FR2797765, EP1261310 and EP1259221 describe the cosmetic use of xanthine to activate lipolysis.

WO2006063714 describes the use of some aryldimethylpyrazolones to prepare formulations suitable for the treatment of cellulite. Aryldimethylpyrazolones had been previously described by Edmondson et al. in Bioorganic & Medicinal Chemistry Letters (2003), 13, 3983-3987, as potent, selective PDE3B inhibitors.

DESCRIPTION OF THE INVENTION

A new aryldimethylpyrazolone derivative has now been found which is surprisingly effective in reducing unsightly cellulite. A first aspect of the invention consequently relates to the compound 5-{4-[2-(4-fluoro-benzyl)-3-oxo-cyclohex-1-enylamine]-2,3-difluoro-phenyl}-4,4-dimethyl-2,4-dihydro-pyrazol-3-one of formula (I):

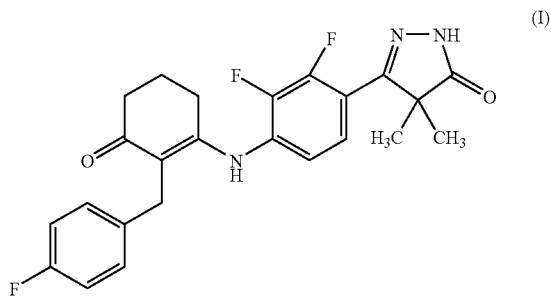

The compound of formula (I) can be salified with cosmetically acceptable acids chosen from among inorganic acids such as hydrochloric, sulphuric or phosphoric acid, or organic acids chosen from among acetic, propionic, succinic, fumaric, lactic, glycolic, citric and tartaric acid.

Another aspect of the invention relates to a cosmetic composition containing the compound of formula (I) as active ingredient, preferably at the concentration of 0.1 to 2% by weight, more preferably 0.1 to 1% by weight, and even more preferably 0.2 to 0.5% by weight.

The compositions according to the invention improve the compactness of the skin and the body tone, minimising the orange-peel appearance and simultaneously moisturising and smoothing the skin, thus visibly improving its elasticity.

Formulations according to the invention can also contain a compound, a mixture of compounds or an extract which are active on the microcirculation, preferably a saponin or flavone, possibly of extractive origin. Extracts of Ginkgo biloba, arnica, pineapple, dong quai (Angelica siniensis), Centella asiatica and the saponin escin are particularly preferred.

The compound, extract or mixture of substances active on the microcirculation can be present in the composition at concentrations ranging between 0.1 and 4%.

The formulations according to the invention can also contain cosmetically acceptable excipients such as adjuvants, in particular water or alcohols (ethanol), vitamins, in particular tocopherol, dexpanthenol or retinol palmitate, thickeners, preservatives, protective colloids, humidifiers, fragrances, electrolytes, moisturisers, gelling agents, agents that increase permeability through the skin, polymers or copolymers, emulsifiers, emulsion stabilisers and other cosmetically acceptable excipients. The topical formulations can contain polyunsaturated fatty acids known as omega 3, including 10-trans-12-cis linoleic acid and docosahexenoic acid.

It is preferable to use hypoallergenic substances such as ethyl alcohol or benzyl alcohol as preservatives.

Particularly suitable gelling agents include carbomer, especially carbomer 940, polyacrylamide isoparaffin-laureth-7, xanthan gum, carrageenan, gum acacia, guar gum, agar gel, alginates and methylhydroxycellulose, carboxymethylcellulose, hydroxypropylcellulose, hydroxypropyl methylcellulose, hydroxyethylcellulose, ethylcellulose, polyacrylates, polyvinyl alcohol, polyvinylpyrrolidone and colloidal silicon dioxide.

Urea and panthenol are examples of moisturisers according to the invention.

The compositions according to the invention may take the form of a gel, spray-gel, cream, non-oily cream, non-oil formulations, ointments or hydroalcoholic lotions.

The techniques for the preparation of the pharmaceutical compositions according to the invention would be known to one skilled in the art, and are described, for example, in Remington's Pharmaceutical Sciences, 18th ed., Mack Publishing Co.

For example, a composition according to the invention in the form of a non-oily cream (100 g) could contain:

|  | % by weight |
| --- | --- |
| Active ingredient: | |
| Compound of formula (I) | 0.2-0.5 |
| escin (optional) | 1-3 |
| Excipients: | |
| (glyceryl monostearate, macrogol cetostearyl ether, liquid paraffin, white vaseline, isopropyl myristate, myristyl alcohol, and p-hydroxybenzoic acid esters) | 20-25 |
| purified water q.s. for | 100 g |

In view of the structural similarity between the compound of formula (I) and other compounds previously described (WO2006063714 and Bioorganic & Medicinal Chemistry Letters (2003), 13, 3983-3987), some comparative tests have been conducted of formulations containing:

A) 3-[2-[4-(4,4-dimethyl-5-oxo-4,5-dihydro-1-H-pyrazol-3-yl)-2,3-difluoro-phenylamine]-6-oxocyclohex-1-enylmethyl]-benzonitrile (hereinafter called "compound A", which corresponds to compound 18n described by Edmondson et al. in Bioorganic & Medicinal Chemistry Letters (2003), 13, 3983-398);

B) 5-{4-[2-(4-fluoro-benzyl)-3-oxo-cyclohex-1-enylamine]-2-fluoro-phenyl}-4,4-dimethyl-2,4-dihydro-pyrazol-3-one (hereinafter called "compound B", which corresponds to compound 18k described by Edmondson et al. in Bioorganic & Medicinal Chemistry Letters (2003), 13, 3983-398);

at the concentration of 0.3% by weight. The cosmetic formulations according to the invention containing the compound of formula (I) have proved significantly more effective in reducing unsightly cellulite.

The following examples illustrate the invention without limiting it in any way.

EXAMPLES

Example 1

Non-oily Cream (% Composition)

Active Ingredient

| | |
| --- | --- |
| Compound of formula (I) | 0.2 |
| escin | 2 |
| Excipients: | |
| glyceryl monostearate | 8 |
| macrogol cetostearyl ether | 2.5 |
| liquid paraffin | 2 |
| white vaseline | 2 |
| isopropyl myristate | 4 |
| myristyl alcohol | 3 |
| p-hydroxybenzoic acid esters | 0.3 |
| purified water q.s. for | 100 g |

Example 2

Non-oily Cream (% Composition)

Active Ingredient

| | |
| --- | --- |
| Compound of formula (I) | 0.3 |
| Excipients: | |
| cetostearyl alcohol | 4.5 |
| glyceryl monostearate | 8.0 |
| liquid paraffin | 2 |
| white vaseline | 2 |
| dimethicone | 0.30 |
| isopropyl myristate | 1 |
| myristic alcohol | 3 |
| essential oils | q.s. |
| purified water q.s. for | 100 g |

Example 3

Non-oily Cream (% Composition)

Active Ingredient

| | |
| --- | --- |
| Compound of formula (I) | 0.5 |
| Excipients: | |
| oleic acid | 5.0 |
| macrogol stearate 40 | 9.0 |
| cetostearyl alcohol | 6.0 |
| butyl hydroxyanisole | 0.02 |
| trometamol | 0.1 |
| dimethicone | 0.3 |
| Carbopol 980 | 0.3 |
| propylene glycol | 20.0 |
| sodium sulphite | 0.1 |
| essential oils | q.s. |
| purified water q.s. for | 100 g |

Example 4

Hydroalcoholic Gel (% Composition)

Active Ingredient

| | |
|---|---|
| Compound of formula (I) | 0.2 |
| Excipients | |
| carbomer | 1.5 |
| 96° ethyl alcohol EP | 40 ml |
| essential oils | q.s. |
| triethanolamine | q.s. to adust pH |
| purified water q.s. for | 100 g |

Example 5

Lipophilic Cream (% Composition)

Active Ingredient

| | |
|---|---|
| Compound of formula (I) | 0.3 |
| Excipients | |
| polyglyceryl-3 diisostearate | 4 |
| glyceryl oleate | 2 |
| beeswax | 7 |
| dicapryl ether | 10 |
| hexyldecanol/hexyldecyl laurate | 10 |
| 85% glycerin | 5 |
| magnesium sulphate 7H$_2$O | 1 |
| p-hydroxybenzoic acid esters | 0.1 |
| essential oils | q.s. |
| purified water q.s. for | 100 g |

Example 6 (Comparative)

Non-oily Cream (% Composition)

Active Ingredient

| | |
|---|---|
| Compound A | 0.3 |
| Excipients: | |
| cetostearyl alcohol | 4.5 |
| glyceryl monostearate | 8.0 |
| liquid paraffin | 2 |
| white vaseline | 2 |
| dimethicone | 0.30 |
| isopropyl myristate | 1 |
| myristic alcohol | 3 |
| essential oils | q.s. |
| purified water q.s. for | 100 g |

Example 7 (Comparative)

Non-oily Cream (% Composition)

Active Ingredient

| | |
|---|---|
| Compound B | 0.3 |
| Excipients: | |
| cetostearyl alcohol | 4.5 |
| glyceryl monostearate | 8.0 |
| liquid paraffin | 2 |
| white vaseline | 2 |
| dimethicone | 0.30 |
| isopropyl myristate | 1 |
| myristic alcohol | 3 |
| essential oils | q.s. |
| purified water q.s. for | 100 g |

Efficacy Test

Cellulite is mainly a cosmetic problem. We therefore examined the cosmetic efficacy of a preparation based on the compound of formula (I) (composition described in example 2) by comparison with a preparation containing product A and product B (compositions described in examples 6 and 7) in reducing unsightly cellulite. Compounds A and B were used as comparators as they are the known compounds most similar to the compound of formula (I).

21 Healthy adult women with evident problems of cellulite in the thigh, hip and buttock areas were divided into three groups. Each group was given a cream chosen from among those described in examples 2, 6 or 7 to be spread on the part of the thigh affected by cellulite and massaged in until absorbed, twice a day every day for two months. The treatment was always to be given on one thigh only so that the other untreated thigh could be used as control. The efficacy of the cosmetic cream was assessed at the end of the period by comparing the treated thigh with the untreated thigh on a 5-point scale. The parameters considered were: reduction of the orange-peel effect, overall appearance of the skin (uniformity and smoothness of the skin, tissue tone and elasticity, moisturisation, considering that of areas distant from those affected by cellulite as ideal), and reduction in thigh circumference. The presence of side effects associated with the treatment, such as redness or itching, was also considered.

The tests clearly demonstrated the satisfaction of the patients treated with the formulation described in example 2, containing the compound of formula (I), which proved much more effective than the formulations described in examples 6 and 7, containing the two comparator compounds.

| | Composition described in example 2 | Composition described in example 6 | Composition described in example 7 |
|---|---|---|---|
| Reduction of orange-peel effect | +++ | + | + |
| Overall appearance | +++ | ++ | ++ |
| Reduction of thigh circumference | ++ | + | + |
| Side effects | + | + | + |

Liquid-crystal thermography was used to conduct an indirect instrumental assessment of the efficacy of the treatment.

On the basis of the surface temperature, this technique distinguishes between normal adipose tissue and tissue affected by cellulite, in which the reduced blood flow causes progressive cooling of the skin, proportional to the severity of the cosmetic problem.

After repeated treatment with compound (I), the difference in temperature between the normal skin area (unaffected by cellulite) and the affected area had reduced considerably, about 70% of the temperature reduction previously observed having been eliminated. The effects of treatment with compounds A and B were evaluated for comparison purposes. Both proved less effective than compound (I), as only some 50% of the temperature difference compared with normal tissue was eliminated.

The invention claimed is:

1. A compound 5-{4-[2-(4-fluoro-benzyl)-3-oxo-cyclohex-1-enylamine]-2,3-difluoro-phenyl}-4,4-dimethyl-2,4-dihydro-pyrazol-3-one with formula (I):

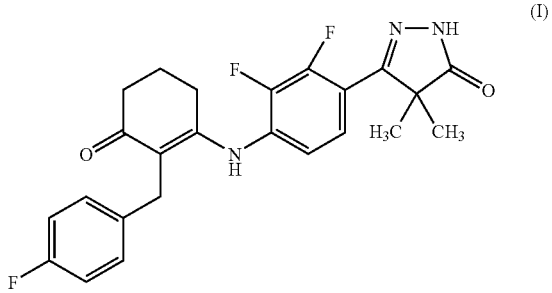

or its cosmetically acceptable salts.

2. A cosmetic composition for topical administration containing the compound of claim 1 or a cosmetically acceptable salt thereof for the treatment of cellulite.

3. The cosmetic composition of claim 2 containing the compound at a concentration of 0.1 to 2% of weight of the composition.

4. The cosmetic composition of claim 2 containing the compound at a concentration of 0.1 to 2% of weight of the composition.

5. The cosmetic composition of claim 2 containing the compound at a concentration of 0.1 to 2% of weight of the composition.

6. The cosmetic composition of claim 2 in a form selected from the group consisting of gel, spray-gel, cream, non-oily cream, non-oil formulations and ointment.

7. The cosmetic composition of claim 2 further comprising a saponin or a flavone extracted from a plant selected from the group consisting of Ginkgo biloba, arnica, pineapple, Angelica sinensis and Centella asiatica.

8. The cosmetic composition of claim 2 further comprising a polyunsaturated omega-3 fatty acid selected from the group consisting of 10-trans-12-cis linoleic acid and docosahexenoic acid.

9. A method for the cosmetic treatment of cellulite comprising administering the cosmetic composition of claim 2 to a patient in need thereof.

10. The cosmetic composition of claim 7, wherein the saponin is escin.

* * * * *